United States Patent
Harks et al.

(10) Patent No.: US 10,765,404 B2
(45) Date of Patent: Sep. 8, 2020

(54) MEDICAL PROBE FOR ULTRASOUND IMAGING

(71) Applicant: KONINKLIJKE PHILIPS N.V., Eindhoven (NL)

(72) Inventors: Godefridus Antoniuss Harks, Eindhoven (NL); Franciscus Johannes Gerardus Hakkens, Eindhoven (NL); Roland Alexander Van De Molengraaf, Eindhoven (NL); Cornelis Petrus Hendriks, Eindhoven (NL); Alexander Franciscus Kolen, Eindhoven (NL); Franciscus Reinier Antonius Van Der Linde, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 298 days.

(21) Appl. No.: 15/768,575

(22) PCT Filed: Oct. 25, 2016

(86) PCT No.: PCT/EP2016/075627
§ 371 (c)(1),
(2) Date: Apr. 16, 2018

(87) PCT Pub. No.: WO2017/072098
PCT Pub. Date: May 4, 2017

(65) Prior Publication Data
US 2018/0296186 A1    Oct. 18, 2018

(30) Foreign Application Priority Data
Oct. 27, 2015   (EP) ..................... 15191572

(51) Int. Cl.
*A61B 8/00* (2006.01)
*A61B 8/12* (2006.01)
(Continued)

(52) U.S. Cl.
CPC .......... *A61B 8/4444* (2013.01); *A61B 8/0841* (2013.01); *A61B 8/12* (2013.01);
(Continued)

(58) Field of Classification Search
USPC .......................................................... 367/7
See application file for complete search history.

(56) References Cited

U.S. PATENT DOCUMENTS

| 5,095,910 A | 3/1992 | Powers |
| 6,781,284 B1 | 8/2004 | Pelrine et al. |

(Continued)

FOREIGN PATENT DOCUMENTS

| JP | H04-92647 A | 3/1992 |
| JP | H04-227239 A | 8/1992 |

(Continued)

OTHER PUBLICATIONS

Fronheiser et al. "Real-Time 3D Color Doppler" (IEEE Trans Ultrason Ferroelectr Freq Control. 2008; 55(6): 1355-1362).
(Continued)

*Primary Examiner* — James R Hulka
(74) *Attorney, Agent, or Firm* — Schott, P.C.

(57) ABSTRACT

An internal probe device for insertion into the body of a patient, comprises an elongate body with a plurality of EAP actuators mounted at the surface of the body. The EAP actuators are made to vibrate so that their position becomes visible in a Doppler ultrasound image. The use of EAP actuators to provide vibrations enables individual locations to be identified. In particular, the movement of the EAP actuator may be largely isolated from the main body of the (Continued)

probe. Furthermore, EAP actuators can be thin, lightweight and have a small form factor suitable for application to or within the surface of a probe, such as a catheter, needle or endoscope.

16 Claims, 2 Drawing Sheets

(51) Int. Cl.
    *A61B 90/00*     (2016.01)
    *A61B 8/08*     (2006.01)
    *G01S 7/52*     (2006.01)
    *G01S 15/89*     (2006.01)

(52) U.S. Cl.
    CPC ............ *A61B 8/4483* (2013.01); *A61B 8/483* (2013.01); *A61B 8/488* (2013.01); *A61B 90/39* (2016.02); *G01S 7/52079* (2013.01); *G01S 15/895* (2013.01); *G01S 15/8936* (2013.01); *G01S 15/8988* (2013.01); *G01S 15/8993* (2013.01); *A61B 2090/3929* (2016.02)

(56) References Cited

U.S. PATENT DOCUMENTS

| | | | | |
|---|---|---|---|---|
| 8,038,621 | B2* | 10/2011 | Baba | A61B 8/0833 324/635 |
| 8,448,644 | B2* | 5/2013 | Hennings | A61B 8/0841 128/898 |
| 8,449,466 | B2* | 5/2013 | Duhay | A61B 8/0841 600/407 |
| 9,356,225 | B2* | 5/2016 | Park | H01L 41/0973 |
| 9,661,998 | B2* | 5/2017 | Yoshino | A61B 1/00133 |
| 2008/0108901 | A1 | 5/2008 | Baba et al. | |
| 2008/0275380 | A1 | 11/2008 | Hennings et al. | |
| 2010/0191175 | A1 | 7/2010 | Couvillon | |
| 2010/0262239 | A1* | 10/2010 | Boyden | A61B 17/68 623/16.11 |
| 2010/0305432 | A1 | 12/2010 | Duhay et al. | |
| 2013/0158390 | A1 | 6/2013 | Tan et al. | |
| 2013/0328447 | A1* | 12/2013 | Park | H01L 41/0973 310/332 |
| 2014/0180089 | A1 | 6/2014 | Alpert et al. | |
| 2014/0180582 | A1* | 6/2014 | Pontarelli | G08B 6/00 701/494 |
| 2014/0276620 | A1 | 9/2014 | Millett et al. | |
| 2015/0374219 | A1 | 12/2015 | Yoshino | |

FOREIGN PATENT DOCUMENTS

| | | |
|---|---|---|
| JP | 2007229266 A | 9/2007 |
| RU | 2521689 C2 | 7/2014 |
| WO | 2014100402 A1 | 6/2014 |
| WO | 2015/004961 A1 | 1/2015 |
| WO | 2015031804 A1 | 3/2015 |

OTHER PUBLICATIONS

T. Shoa et al., "Conduct-ing polymer actuator driven catheter: over-view and applications", SPIE, 72871J1-9, 2009.

* cited by examiner

MEDICAL PROBE FOR ULTRASOUND IMAGING

CROSS-REFERENCE TO PRIOR APPLICATIONS

This application is the U.S. National Phase application under 35 U.S.C. § 371 of International Application No. PCT/EP2016/075627, filed on Oct. 25, 2016, which claims the benefit of EP Patent Application No. EP 15191572.5, filed on Oct. 27, 2015. These applications are hereby incorporated by reference herein.

FIELD OF THE INVENTION

This invention relates to medical imaging devices, and in particular systems for viewing the position of internal probes used during a surgical or investigative procedure, using ultrasound.

BACKGROUND OF THE INVENTION

Ultrasound is often used as a tool to guide surgical devices like needles or catheters during minimally invasive procedures. For example, surgical biopsy procedures are commonly performed using ultrasonic imaging to enable the physician to view the tissue being biopsied.

One of the advantages of ultrasound over X-ray imaging for use during a surgical procedure is that it provides soft tissue contrast and depth information, while it does not use ionizing radiation. However, it is often challenging to identify interventional devices in an ultrasound image since many devices such as needles are specular reflectors and do not return the ultrasound beam back to the transducers.

In addition, devices such as catheters may have a similar appearance on ultrasound images as tissue structures, also depending on imaging settings. Various techniques are used to improve the visualization of devices, such as adding echogenic coatings or etching.

The concept of needle tracking in an ultrasound device is known, for example by coating a needle tip with a piezo-material that provides an electrical signal upon "activation" by ultrasound energy. An ultrasonic transducer may alternatively be attached to a biopsy needle to cause the needle to transmit and/or receive ultrasonic waves in cooperation with an imaging scan head.

An alternative to these active approaches is to passively view the biopsy needle using color Doppler images. Hand manipulation of a biopsy needle or guide-wire has been found to provide a color image that corresponds to the shaft of the needle. However, the image of the needle is only highly defined when the needle is being manipulated, and is a coarse representation of the entire needle shaft.

It has been proposed to continually visualize the tip of the needle by mechanically reciprocating the needle. Unsynchronized reciprocation of the biopsy needle (or stylet) causes a constantly changing Moiré pattern when the Doppler representation of the needle tip is displayed in color. A system making use of this technique is described in U.S. Pat. No. 5,095,910.

US2010/0305432 discloses another system and method for locating medical devices in vivo using ultrasound in a 3D Doppler mode. In this method, 3D Doppler imaging is used to detect a medical device coupled to a vibratory element to induce vibrations in the distal end of the device. Different parts of the medical device may be configured to vibrate with different frequencies. This is achieved by segments of material of different densities, which attenuate the vibrations generated by a vibration module at the proximal end.

The concept of vibrational device detection using Real-Time 3D Color Doppler has also been proposed in IEEE Trans Ultrason Ferroelectr Freq Control. 2008; 55(6): 1355-1362.

Various different uses of vibration elements have been proposed, for use in Doppler imaging systems, such as:

providing a vibrating element to a minimally invasive device (catheter, needle, guide-wire) to provide whole body vibrations;

providing a vibrating element at a proximal end (ex vivo) or distal end (in vivo);

using different frequencies at different locations, for example with the frequency altered by changes in material density or more vibrating elements.

SUMMARY OF THE INVENTION

These known vibratory elements, described hereinbefore, for minimally invasive healthcare devices based on Doppler tracking vibrate the complete cross section of a device. As a result, different areas influence each other and the spatial information density is quite limited due to cross talk. Many medical devices are symmetrical (needles, catheters) and orientation information of the device is lost if only a point is tracked.

There is therefore a need for an improved technique for imaging a probe within an ultrasound image.

The aforementioned goal is at least partially achieved with the invention defined by the independent claims. The dependent claims provide advantageous embodiments.

According to examples in accordance with an aspect of the invention, there is provided a probe device for insertion into the body of a patient, comprising:
an elongate body;
a plurality of EAP actuators mounted at or integrated in the surface of the elongate body; and
a controller adapted to control the EAP actuators thereby to cause them to provide a vibration at a frequency not exceeding 5 kHz.

The invention provides a system and method for providing vibration of a probe, for use in tracking of the vibrations using Doppler imaging. Instead of fixing a vibrational element to the probe, a plurality of electro-active polymer elements are attached to, or embedded in, the probe device. The device can be a so called "internal" device for insertion into the body of a subject. The subject can be a living subject or a lifeless subject. It may be any subject that can accommodate the probe device within its body (i.e. that can be internally investigated or examined with such a probe device). Preferably the probe device is a device for insertion into the body of a human or animal. The device can thus be a medical device such as a needle, catheter, sheath, guide-wire or endoscope, or the like. The device can then be suitably monitored or imaged using an ultrasound device.

The EAP actuators may be integrated into the device wall, and they may be thin, flexible and/or bendable.

By providing local EAP actuators, they are able to vibrate only a section of the outer wall of the probe device and not the complete device. Hence they can provide the vibration only locally. In this way, they may operate independently with less influence of cross talk, thereby enabling a higher spatial resolution, and thus higher information density.

By using electro-active polymer actuators, thin, flexible, high stroke elements operating in the Hz-MHz range can be integrated in or on the device wall. In this way, segments over the circumference can be made to vibrate rather than a complete device. More segments can be integrated in a cross section of the device. This has a number of benefits such as being able to determine the 3D orientation of the probe (for example projecting in or out of the imaging plane) as well as determining the distance from the distal and/or proximal end.

By using EAP actuators, larger areas can be actuated while keeping the device flexible.

The controller is for example adapted to apply a vibration frequency in the range 5 Hz to 5 kHz. This is a frequency range suitable for EAP actuators and suitable for enabling detection and visualization of the elongate body by Doppler ultrasound imaging. Since the invention is for visualizing and/or tracking the elongate body by Doppler ultrasound imaging, the frequency of vibration should in all cases be suitable for enabling this functionality.

A maximum operation frequency of around 5 kHz is appropriate for example when the taking into account the maximum resolution (i.e. the smallest displacement that can be imaged) and the response frequency of ultrasound.

More typically, frequencies may be in the range 5 Hz to 1 kHz, for example 10 Hz to 1 kHz, for example 50 Hz to 1 kHz. High frequencies of operation may also be undesirable from a signal processing point of view. Hence, the upper limit of 1 kHz in the ranges above may be 750 Hz, or 500 Hz or 250 Hz. High frequencies may also be undesirable from the point of view of image quality.

In some cases, a frequency of vibration may be even lower, for example in the range 0.5 Hz to 10 Hz.

According to some examples, the actuators may be controlled to implement a pulsing operation, wherein the actuators perform single or discrete pulses followed by a certain waiting time. In this case, 'vibration frequency' may refer to an effective vibration frequency, meaning a frequency of pulsation. In these cases, the vibration frequency may be lower, for example even lower than 0.5 Hz.

The controller is for example adapted to apply a different vibration frequency to at least two different EAP actuators. Different vibration frequencies will show up as different colors in a 3D color Doppler image.

The vibration may be induced locally in a radial direction (with respect to the body of the probe device) in at least some of the EAP actuators. For example, the EAP actuator may bow radially inwardly and outwardly.

The vibration may be induced locally in an axial direction (with respect to the body of the probe device) in at least some of the EAP actuators. For example, the EAP actuators may stretch and contract in the axial direction.

The vibration may be induced locally in a tangential direction (with respect to the body of the probe device) in at least some of the EAP actuators. For example, the EAP actuator may stretch and contract around a circumference of the probe.

A combination of any of the above directions of vibration is also possible. Many different other configurations are also possible.

A first sub-set of EAP actuators may be at one angular position around the elongate body and a second sub-set of EAP actuators may be at another angular position around the body.

By placing different elements around the circumference, with their own characteristic vibration frequency, it becomes possible to identify a 3D orientation using a 2D image plane, for example to determine the direction of the tip.

Different elements may also be placed at different distance from the tip or from other regions of interest, so that a distance from the tip or other region is indicated.

Rotational orientation information may also be provided, again based on different actuators at different circumferential positions.

The controller may be adapted to control the EAP actuators thereby to induce steering of a tip of the probe. A first sub-set of the EAP actuators may be for steering control and a second sub-set of the EAP actuators may be for vibration control. At least one EAP actuator may be for both steering control vibration control.

In this way, the EAP actuators can together be used for Doppler ultrasound tracking (vibration) as well as device steering (bending) at the same time, enabling integration of both functions in a single element using the same technology.

The device for example comprises a catheter. The EAP actuators may be integrated into an outer wall of the device.

Examples in accordance with another aspect of the invention provide system, comprising:

a probe device as defined above;

an ultrasound scanner adapted to be operated in a 3D Doppler mode, wherein the ultrasound scanner is adapted to generate 3D Doppler data.

The probe device is thus adapted to provide the vibrations that can be sensed by the ultrasound scanner when operating in the 3D Doppler mode.

The system preferably is an imaging system and even more preferably is a medical imaging system.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
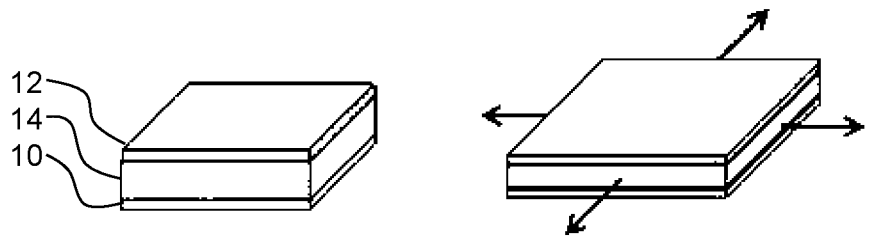
FIG. 1 shows a known electro-active polymer device which is not clamped.

The invention provides an internal probe device for insertion into the body of a patient, comprising an elongate body with a plurality of EAP actuators mounted at the surface of the body. The EAP actuators are made to vibrate so that their position becomes visible in a Doppler ultrasound image.

As discussed above, the use of vibration to make a feature visible in a Doppler ultrasound image is known. The use of EAP actuators for this purpose enables individual locations to be identified. In particular, the movement of the EAP actuator may be largely isolated from the main body of the probe. Furthermore, EAP actuators can be thin, lightweight and have a small form factor suitable for application to or within the surface of a probe, such as a catheter, needle or endoscope.

Electro-active polymer (EAP) technology will first be discussed.

Electro-active polymers (EAPs) are an emerging class of materials within the field of electrically responsive materials. EAPs can work as sensors or actuators and can easily be manufactured into various shapes allowing easy integration into a large variety of systems.

Materials have been developed with characteristics such as actuation stress and strain which have improved significantly over the last ten years. Technology risks have been reduced to acceptable levels for product development so that EAPs are commercially and technically becoming of increasing interest. Advantages of EAPs include low power, small form factor, flexibility, noiseless operation, accuracy, the possibility of high resolution, fast response times, and cyclic actuation.

The improved performance and particular advantages of EAP materials give rise to applicability to new applications.

An EAP device can be used in any application in which a small amount of movement of a component or feature is desired, based on electric actuation. Similarly, the technology can be used for sensing small movements. This application however makes use only of the actuator function.

The use of EAPs enables functions which were not possible before, or offers a big advantage over common sensor/actuator solutions, due to the combination of a relatively large deformation and force in a small volume or thin form factor, compared to common actuators. EAPs also give noiseless operation, accurate electronic control, fast response, and a large range of possible actuation frequencies, such as 0-1 MHz, typically below 20 kHz.

Devices using electro-active polymers can be subdivided into field-driven and ionic-driven materials.

Examples of field-driven EAPs include Piezoelectric polymers, Electrostrictive polymers (such as PVDF based relaxor polymers) and Dielectric Elastomers. Other examples include Electrostrictive Graft polymers, Electrostrictive paper, Electrets, Electroviscoelastic Elastomers and Liquid Crystal Elastomers.

Examples of ionic-driven EAPs are conjugated/conducting polymers, Ionic Polymer Metal Composites (IPMC) and carbon nanotubes (CNTs). Other examples include ionic polymer gels.

Field-driven EAPs are actuated by an electric field through direct electromechanical coupling. They usually require high fields (volts per meter) but low currents. Polymer layers are usually thin to keep the driving voltage as low as possible. Ionic EAPs are activated by an electrically induced transport of ions and/or solvent. They usually require low voltages but high currents. They require a liquid/gel electrolyte medium (although some material systems can also operate using solid electrolytes).

Both classes of EAP have multiple family members, each having their own advantages and disadvantages.

A first notable subclass of field driven EAPs are Piezoelectric and Electrostrictive polymers. While the electromechanical performance of traditional piezoelectric polymers is limited, a breakthrough in improving this performance has led to PVDF relaxor polymers, which show spontaneous electric polarization (field driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field driven EAPs is that of Dielectric Elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

A first notable subclass of ionic EAPs is Ionic Polymer Metal Composites (IPMCs). IPMCs consist of a solvent swollen ion-exchange polymer membrane laminated between two thin metal or carbon based electrodes and requires the use of an electrolyte. Typical electrode materials are Pt, Gd, CNTs, CPs, Pd. Typical electrolytes are Li+ and Na+ water-based solutions. When a field is applied, cations typically travel to the cathode side together with water. This leads to reorganization of hydrophilic clusters and to polymer expansion. Strain in the cathode area leads to stress in rest of the polymer matrix resulting in bending towards the anode. Reversing the applied voltage inverts bending. Well known polymer membranes are Nafion® and Flemion®.

Another notable subclass of Ionic polymers is conjugated/conducting polymers. A conjugated polymer actuator typically consists of an electrolyte sandwiched by two layers of the conjugated polymer. The electrolyte is used to change oxidation state. When a potential is applied to the polymer through the electrolyte, electrons are added to or removed from the polymer, driving oxidation and reduction. Reduction results in contraction, oxidation in expansion.

In some cases, thin film electrodes are added when the polymer itself lacks sufficient conductivity (dimension-wise). The electrolyte can be a liquid, a gel or a solid material (i.e. complex of high molecular weight polymers and metal salts). Most common conjugated polymers are polypyrolle (PPy), Polyaniline (PANi) and polythiophene (PTh).

An actuator may also be formed of carbon nanotubes (CNTs), suspended in an electrolyte. The electrolyte forms a double layer with the nanotubes, allowing injection of charges. This double-layer charge injection is considered as the primary mechanism in CNT actuators. The CNT acts as an electrode capacitor with charge injected into the CNT, which is then balanced by an electrical double-layer formed by movement of electrolytes to the CNT surface. Changing the charge on the carbon atoms results in changes of C—C bond length. As a result, expansion and contraction of single CNT can be observed.

Figure 2:
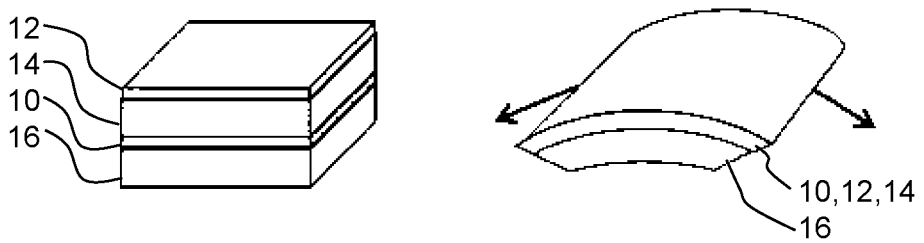
FIG. 2 shows a known electro-active polymer device which is constrained by a backing layer.

FIGS. 1 and 2 show two possible operating modes for an EAP device.

The device comprises an electro-active polymer layer 14 sandwiched between electrodes 10, 12 on opposite sides of the electro-active polymer layer 14.

FIG. 1 shows a device which is not clamped. A voltage is used to cause the electro-active polymer layer to expand in all directions as shown.

FIG. 2 shows a device which is designed so that the expansion arises only in one direction. The device is supported by a carrier layer 16. A voltage is used to cause the electro-active polymer layer to curve or bow.

The nature of this movement for example arises from the interaction between the active layer which expands when actuated, and the passive carrier layer. To obtain the asymmetric curving around an axis as shown, molecular orientation (film stretching) may for example be applied, forcing the movement in one direction.

The expansion in one direction may result from the asymmetry in the EAP polymer, or it may result from asymmetry in the properties of the carrier layer, or a combination of both.

Figure 3:
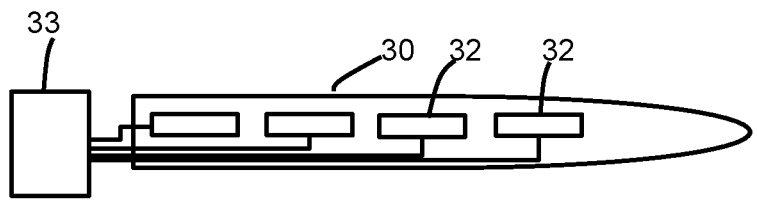
FIG. 3 shows a first example of a catheter with EAP vibration elements.

FIG. 3 shows a probe 30 with a set of EAP actuators 32 arranged along its length. The probe is a minimally invasive healthcare device such as a catheter, sheath, guide-wire, needle, or endoscope. The EAP actuators are to provide vibration for ultrasound Doppler imaging. The actuators 32 are controlled by a controller 33 outside the probe, at the proximal end.

The electro-active polymer actuators 32 are either provided on the outside of the outer housing of the probe or they may be integrated into the structure of the outer wall.

In a first example, the EAP actuators are bending actuators, i.e. they deform out of plane. In one implementation, each actuator comprises a field driven EAP layer sandwiched between two electrodes and a passive substrate. The substrate is optional, and the body of the probe may function as the substrate for the EAP actuator.

The actuators may instead deform in plane. The vibration may then be in a tangential direction in a plane perpendicular to the length of the probe, or else it may be in a direction parallel to the length axis of the probe. It may be in all directions in plane (as in FIG. 1).

Any combination of radial, longitudinal and circumferential vibration can be used.

If in-plane vibration is used, the actuator is preferably isolated, for example surrounded by a clearance, so that the vibrations do not couple significantly into the main body of the probe. Alternatively, the material around the EAP has some flexibility in the vibration (longitudinal or tangential) direction to provide damping of the vibrations before they couple into the remainder of the probe.

A controller is used to drive the EAP actuators. Different vibration frequencies are visualized differently in a Doppler ultrasound image, for example as different colors. Thus, different EAP actuators may be operated at different frequencies in order to make different locations of the probe distinguishable in the ultrasound image. Alternatively, or additionally, different EAP actuators can be coded using differences, size, time delay, phase shift, geometrical spacing between different elements or a motion pattern applied to the vibration sequence.

By having discrete actuators rather than vibrating the whole of the probe, the orientation and direction of the probe can be visualized.

Figures 4A, 4B:
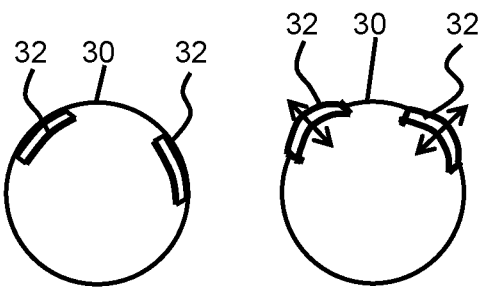
FIG. 4(a) shows a second example of a probe with EAP vibration elements, in a flat state, positioned at different locations around the circumference of the probe.
FIG. 4(b) shows a second example of a probe with EAP vibration elements, in a driven bulged state, positioned at different locations around the circumference of the probe.

FIGS. 4(a) and 4(b) shows that EAP actuators 32 may be positioned at different locations around the circumference of the probe 30. By having independent elements over the circumference of the device, and by ensuring minimum cross talk, high spatial resolution is possible, thereby giving rotational orientation information.

FIG. 4(a) shows two EAP actuators 32 at different angular positions, and in a flat state. FIG. 4(b) shows the two EAP actuators 32 in a driven bulged state. As shown, in this example the EAP actuators vibrate in a radial direction, i.e. inwardly and outwardly.

By way of example, in an image which is a cross section across the length of the probe, the relative positions of the two EAP actuators around the circumference gives an indication of the direction in which the probe is pointing (into the image or out of the image). For example when one EAP actuator is clockwise of the other (assuming they are not diametrically opposite), the probe is directed into the image, and when the one EAP actuator is counter-clockwise of the other the probe is directed out of the image. In this way, some 3D information is provided in a 2D imaging plane. The different EAP actuators again are vibrated at different frequencies to enable one to be distinguished from the other.

The individual identification of the EAP actuators also enables information to be derived about the distance to the distal and/or proximal end of the probe, or other features. For example, if only one EAP actuator is visible in a particular image, its identification enables the position along and/or around the probe to be determined.

The angular distance between the two actuators shown in FIGS. 4(a) and 4(b) can also contain information about the distance from the distal tip of the imaging plane. For example, the angular spacing may become smaller towards the tip.

Distance information can also be derived from the other variable parameters described above, such as frequency, size, time delay, motion pattern etc.

Rotational orientation is also obtained from the Doppler image when a circumferential arrangement of EAP actuators is provided.

Coded Doppler sequences may also be used. These would take the form of a vibration frequency which is modulated at a lower frequency to encode a data signal.

Algorithms may then be used to decipher such coded Doppler sequences. Such coding enables the position and rotation of the catheter to be determined in the same way as described above by uniquely identifying EAP actuators so they can be automatically recognized. It also enables other information to be provided to the ultrasound imaging system, such as the type of probe. For example, with information about a catheter such as the diameter, material type, etc. provided to the ultrasound system, it becomes possible to provide automated image optimization.

The Doppler system parameters can be optimized to visualize the moving parts of the device or else the motion that is induced in the surrounding tissue (example blood).

Figure 5:
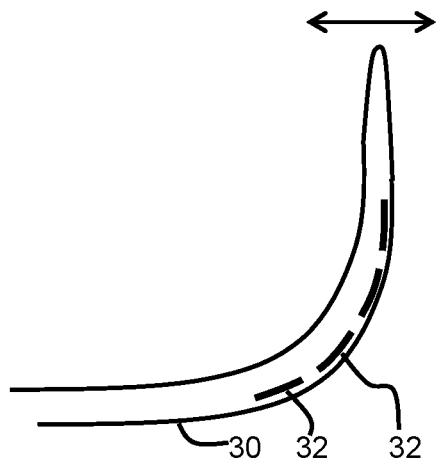
FIG. 5 shows how EAP actuators may be used for steering and for vibration.

FIG. 5 shows a catheter 30 with an arrangement of EAP actuators 32 which enable a bending to be induced, thereby providing a steerable device, as well as providing vibration for Doppler ultrasound tracking. Steering may be applied to a catheter, sheath, or guide-wire.

A vibration may be provided at the tip with steering control along the shaft. Alternatively, the EAP actuators may be controlled with a slowly varying signal for steering onto which is superposed a higher frequency signal to induce vibrations. Thus, individual EAPs may perform the function of both steering control and vibration control.

For EAP actuators designed to provide vibrations which will be visible in the Doppler ultrasound image, there are various design parameters which can be adopted.

The ultrasound Doppler imaging measures velocity, and is for example effective in the range −120 cm/s to +120 cm/s.

By way of example, a typical catheter diameter may be 1 mm (e.g. size 3 of the French Catheter Scale). For the examples of FIGS. 4(*a*) and 4(*b*), assuming a diameter of 1 mm, the maximum displacement radially outwardly may have a magnitude of 0.1 mm (=0.01 cm). Thus, the deformation may be approximated by a sine wave $0.01 \sin(2\pi ft)$. The velocity is $0.02 \pi f \cos(2 \pi ft)$. Setting the maximum velocity to 120 cm/s yields f=1909 Hz. Setting a higher maximum velocity and/or a smaller maximum displacement yields a higher frequency. A maximum displacement of 0.5 mm (=0.005 cm) yields a frequency of around 4 kHz.

A maximum operation frequency of around 5 kHz is appropriate when the taking into account the maximum resolution (i.e. the smallest displacement that can be imaged) and the response frequency of ultrasound.

For a larger EAP actuator displacement, a smaller frequency will reach the typical maximum sensitivity of the Doppler imaging system. Furthermore, the maximum velocity does not need to reach the maximum detectable velocity, and a maximum tip velocity in the range 1 cm/s to 100 cm/s may be used, or even 1 cm/s to 50 cm/s.

Typically, the frequency of operation will be in the range of 5 Hz to 5 kHz, more preferably 5 Hz to 1 kHz, for example 10 Hz to 1 kHz, for example 50 Hz to 1 kHz. High frequencies of operation may also be undesirable from a signal processing point of view. Hence, the upper limit of 1 kHz in the ranges above may be 750 Hz, or 500 Hz or 250 Hz.

The EAP actuators for generating a vibration do not need to have a large actuation sweep, and are therefore typically smaller than would be used for steering. One example of peak to peak displacement of 0.01 cm has been given above (0.1 mm). A larger size of tip movement may be more easily detectable, so a suitable range of EAP actuator peak to peak displacement values is 0.05 mm to 5 mm, such as 0.1 mm to 2 mm.

The EAP actuators for vibration do not need to be long, as is the case for bending actuators. They may have a unity aspect ratio, by which is meant they are the same length and width (in the plane of the layers). Thus, they may be circular, square or any regular polygon, or indeed any other suitable shape. They may have an aspect ratio up to 5:1 and still be designed specifically for the Doppler vibration aspect.

As explained above, there may also be steering actuators. These are typically longer (i.e. with a greater aspect ratio, for example more than 5:1) but they may also be induced to vibrate at the frequencies explained above, for example superposed over a slower time-varying steering control signal.

Thus an EAP actuator may be provided with a time-varying control signal to cause and control bending with a lower frequency than a superposed vibration frequency. The frequency of the signal for controlling bending may be in the range 0.5 Hz to 10 Hz.

A complete system may have at least one EAP actuator designed specifically for Doppler vibration imaging, with the frequency ranges, aspect ratio, and displacement ranges explained above, The system may then have further EAP actuators for steering but which are additionally driven to vibrate. There may even be separate steering actuators which are not induced to vibrate.

The size of the EAP actuators for vibration Doppler imaging may also be very small. For example, if the catheter of FIG. 4 has a diameter of 1 mm, and therefore a circumference of 3.14 mm, each actuator should occupy less than 25% of the circumferential distance, for example less than 0.7 mm. The French Gauge for catheter sizes reaches 3.33 mm diameter (size 10). The EAP actuator for example has a smallest dimension in the range 0.2 mm to 5 mm, for example 0.2 to 2 mm. For a unity aspect ratio design, both dimensions (length and width) will of course be in this range. For a steering and vibration actuator, it may be much more elongate, for example 5 mm×50 mm.

As mentioned above, by using locally embedded or attached EAP actuators, actuators are able to vibrate only local sections of the outer wall of the probe device, and not the complete device. This enables individual sections of the probe wall to be identified from one another in a Doppler ultrasound image, and, as a result, greater spatial resolution and information density achieved in the images of the probe. In particular, greater angular information is obtained, which enables 3D orientation of the probe to be more easily determined.

To ensure high resolution in the orientational information, it is desirable in embodiments to ensure that vibrations generated by each EAP actuator are kept as local as possible, and largely isolated from the remainder of the probe body. Where different actuators are embedded or attached at different circumferential sections of the probe wall for instance, it is desirable to keep vibrations of each actuator confined to its own local wall section, and isolated from remaining wall sections. This vibrational insularity or isolation ensures that cross-talk between actuator vibrations is minimized or largely eliminated, thus allowing spatial resolution of the resulting Doppler images to be maximized.

EAPs are intrinsically suited to achieving such independent vibrational operation. This is at least in part due to their lightweight, thin, and flexible form factor, which enables induced vibrations to be applied extremely precisely to highly localized sections or areas of a given carrying body (i.e. the probe in this case).

In addition, in accordance with at least a subset of embodiments, further structural adaptations may be performed to bolster the vibrational insularity of each EAP actuator. A number of different approaches are possible.

In accordance with at least a first subset of example embodiments, EAP actuators for inducing vibrations may be located in closer proximity to a lower-stiffness distal end of the probe than to a high stiffness proximal end. In particular in the case of probes having steering capability, such as the example illustrated in FIG. 5, the steering distal end will typically be composed of a more flexible, elastic material composition than the non-steering proximal end of the probe. The two ends may be composed of the same material in differing densities (the distal end having lower density) or may be composed of different materials or different material compositions.

By mounting or embedding EAP actuators within the wall of the probe close to (or actually within) the bendable, flexible distal section of the probe shaft, vibrations of each actuator are largely dampened by the proximate (or surrounding) more flexible material. In particular, vibrations travelling at least toward the distal end are dampened by the more flexible material, hence at least reducing the total vibrational energy free to propagate to other areas of the probe (for example the wall sections being vibrated by other actuators). This hence reduces cross-talk between different vibrating sections, and helps enhance spatial resolution of obtained Doppler ultrasound images.

In accordance with at least a second subset of embodiments, EAP actuators may be covered or encased by a deformable low-stiffness material layer to substantially absorb or dampen propagation of vibration into the body of the probe. An example of such an arrangement is shown by way of illustration in FIGS. 6(a) and 6(b) which show a cross-section of an example probe 30 having EAP actuators 32 embedded in an outer section of the probe wall at two different circumferential locations. Each of the EAP actuators 32 is covered across an upper major surface with a layer 38 of flexible, low-stiffness material.

Figure 6A:
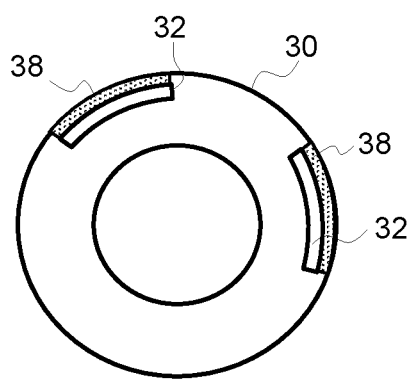
FIG. 6(a) shows a cross-section of an example probe having EAP actuators, in an inactive and/or flat state, embedded in an outer section of the probe wall at two different circumferential locations.
Figure 6B:
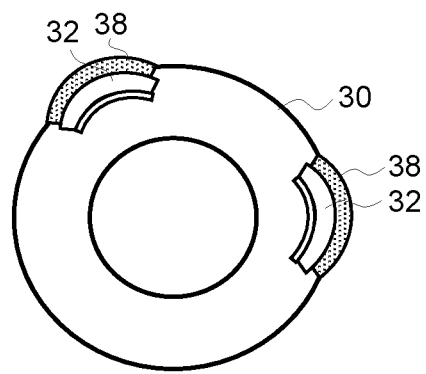
FIG. 6(b) shows a cross-section of an example probe having EAP actuators, in an actuated and/or deformed shape, embedded in an outer section of the probe wall at two different circumferential locations.

FIG. 6(a) shows the actuators in an inactive, flat state. FIG. 6(b) shows the actuators in an actuated, deformed shape. The absorbent, flexible layer 38 is coupled to the EAP actuator 32 such that it follows the movement and deformation of the actuator and the two bend and move together.

The flexible layer 38 has the effect of absorbing or dampening vibrations produced by the EAP actuator 32, to weaken or prevent vibrational transference into the surrounding probe body, or the surrounding sections of the probe wall. This hence prevents cross-talk between different EAP actuators, and different wall sections, thereby enhancing spatial resolution and information density, and improving detection of orientation.

Although in the example of FIGS. 6(a) and 6(b), the actuators are covered across only a single surface, in alternative examples, the actuator may be covered on more than one surface, or may be encased in a low-stiffness material.

According to at least a third subset of embodiments, the EAP actuators may be driven at particular frequencies selected to prevent substantial vibration of the surrounding probe or catheter body. In particular, the actuators may be driven to vibrate at a frequency which is greater than the resonance frequency of the main probe, catheter body, or catheter body segment. This hence avoids the case of inducing resonance in the probe, and hence the occurrence of high-amplitude vibrations across the entire probe body.

The resonance frequency of the probe or actuator will depend upon the particular dimensions and construction of the device, in particular upon the elasticity or stiffness of the material, and the length of the body. In the case that the EAP actuators are to be embedded in the flexible distal (tip) part of the probe or catheter body, this part may typically have a resonance frequency of approximately 10 Hz (although this will vary widely for different materials and dimensional variations). The EAP actuator vibration frequency may, in examples, be selected to be at least two times the resonance frequency of the portion of the probe or catheter within or on which it is embedded or attached.

Each of these three approaches to reducing vibrational cross-talk may be advantageously combined together, to further improve localization and insulation of each EAP actuator.

Materials suitable for the EAP layer are known. Electro-active polymers include, but are not limited to, the sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The sub-class dielectric elastomers includes, but is not limited to:

acrylates, polyurethanes, silicones.

The sub-class conjugated polymers includes, but is not limited to:

polypyrrole, poly-3,4-ethylenedioxythiophene, poly(p-phenylene sulfide), polyanilines.

Ionic devices may be based on ionic polymer-metal composites (IPMCs) or conjugated polymers. An ionic polymer-metal composite (IPMC) is a synthetic composite nanomaterial that displays artificial muscle behavior under an applied voltage or electric field.

In more detail, IPMCs are composed of an ionic polymer like Nafion or Flemion whose surfaces are chemically plated or physically coated with conductors such as platinum or gold, or carbon-based electrodes. Under an applied voltage, ion migration and redistribution due to the imposed voltage across a strip of IPMCs result in a bending deformation. The polymer is a solvent swollen ion-exchange polymer membrane. The field causes cations travel to cathode side together with water. This leads to reorganization of hydrophilic clusters and to polymer expansion. Strain in the cathode area leads to stress in rest of the polymer matrix resulting in bending towards the anode. Reversing the applied voltage inverts the bending.

If the plated electrodes are arranged in a non-symmetric configuration, the imposed voltage can induce all kinds of deformations such as twisting, rolling, torsioning, turning, and non-symmetric bending deformation.

In all of these examples, additional passive layers may be provided for influencing the electrical and/or mechanical behavior of the EAP layer in response to an applied electric field.

The EAP layer of each unit may be sandwiched between electrodes. The electrodes may be stretchable so that they follow the deformation of the EAP material layer. Materials suitable for the electrodes are also known, and may for example be selected from the group consisting of thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS). Metalized polyester films may also be used, such as metalized polyethylene terephthalate (PET), for example using an aluminum coating.

The invention is of interest generally for invasive medical devices such as catheters, sheathes, guide-wires, needles and endoscopes. It is for use in ultrasound image guided therapy systems in combination with ultrasound Doppler tracking.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A probe device comprising:
    an elongate body;
    a plurality of electro-active polymer actuators mounted at the surface of the elongate body; and
    a controller circuit, wherein the controller circuit is arranged to control a vibration of the plurality of electro-active polymer actuators,
    wherein the vibration frequency is less than or equal to 5 kHz.

2. The probe device as claimed in claim 1, wherein the vibration is induced locally in a radial direction in at least two of the plurality of electro-active polymer actuators.

3. The probe device as claimed in claim 1, wherein the vibration is induced locally in an axial direction in at least two of the plurality of electro-active polymer actuators.

4. The probe device as claimed in claim 1, wherein a first sub-set of the plurality of electro-active polymer actuators are at one angular position around the elongate body and a second sub-set of the plurality of electro-active polymer actuators are at another angular position around the elongate body.

5. The probe device as claimed in claim 1, wherein the vibration frequency is greater than a resonance frequency of the elongate body.

6. The probe device as claimed in claim 1, wherein at least a portion of at least one of the plurality of electro-active polymer actuators is covered by a vibration dampening layer.

7. The probe device as claimed in claim 1, wherein the controller circuit is arranged to apply a different vibration frequency to at least two different electro-active polymer actuators of the plurality of electro-active polymers actuators.

8. The probe device as claimed in claim 1, wherein the controller circuit is arranged to apply a coded vibration sequence to at least one of the plurality of electro-active polymer actuators.

9. The probe device as claimed in claim 1, wherein the controller circuit is arranged to control the plurality of electro-active polymer actuators to induce steering of a tip of the probe device.

10. The probe device as claimed in claim 9, wherein a first sub-set of the plurality of electro-active polymer actuators are arranged for steering control and a second sub-set of the plurality of electro-active polymer actuators are arranged for providing the vibration.

11. The probe device as claimed in claim 9, wherein at least one of the plurality of electro-active polymer actuators is arranged to provide steering and the vibration.

12. A catheter comprising the probe device as claimed in claim 1.

13. An imaging system, comprising:
a probe device, for insertion into the body of a subject, as claimed in claim 1; and
an ultrasound scanner,
wherein the ultrasound scanner is arranged to operate in a 3D Doppler mode,
wherein the ultrasound scanner is arranged to generate 3D Doppler data.

14. The imaging system as claimed in claim 13, wherein the imaging system is a medical imaging system for imaging a part of a human or animal body.

15. The probe device as claimed in claim 1, wherein the vibration is induced locally in a tangential direction in at least two of the plurality of electro-active polymer actuators.

16. A probe device, comprising:
an elongate body;
a plurality of electro-active polymer actuators integrated into an outer wall of the probe device; and
a controller circuit, wherein the controller circuit is arranged to control a vibration of the plurality of electro-active polymer actuators, and
wherein the vibration frequency is less than or equal to 5 kHz.

* * * * *